United States Patent
Shah (10) Patent No.: US 12,230,408 B1
(45) Date of Patent: Feb. 18, 2025

(54) GENERATING A MEDICAL KNOWLEDGE PACKET IN AN ACTIVE CONVERSATION SESSION

(71) Applicant: Sandeep Navinchandra Shah, Northborough, MA (US)

(72) Inventor: Sandeep Navinchandra Shah, Northborough, MA (US)

(73) Assignee: Sandeep Navinchandra Shah, Northborough, MA (US)

( * ) Notice: Subject to any disclaimer, the term of this patent is extended or adjusted under 35 U.S.C. 154(b) by 20 days.

(21) Appl. No.: 18/228,932

(22) Filed: Aug. 1, 2023

(51) Int. Cl.
| | |
|---|---|
| *G16H 80/00* | (2018.01) |
| *G06F 40/40* | (2020.01) |
| *G16H 10/60* | (2018.01) |
| *G16H 20/00* | (2018.01) |
| *G16H 70/00* | (2018.01) |

(52) U.S. Cl.
CPC ............ *G16H 80/00* (2018.01); *G06F 40/40* (2020.01); *G16H 10/60* (2018.01); *G16H 20/00* (2018.01); *G16H 70/00* (2018.01)

(58) Field of Classification Search
CPC ........ G16H 10/60; G16H 20/00; G16H 50/20; G16H 70/00; G16H 70/20; G16H 70/40; G16H 70/60; G06F 40/40
See application file for complete search history.

(56) References Cited

U.S. PATENT DOCUMENTS

| | | | | |
|---|---|---|---|---|
| 2009/0062623 A1* | 3/2009 | Cohen | ................... | G16H 70/60 600/300 |
| 2009/0070147 A1* | 3/2009 | Kashani | ................. | G16H 40/63 705/3 |
| 2012/0078837 A1* | 3/2012 | Bagchi | ................ | G06F 16/2428 706/52 |

(Continued)

FOREIGN PATENT DOCUMENTS

| | | | | |
|---|---|---|---|---|
| CA | 2585957 A1 | * | 10/2008 | ............ G06F 19/00 |
| CN | 109817351 A | | 5/2019 | |
| CN | 111680499 A | | 9/2020 | |

OTHER PUBLICATIONS

Kim, Jin K., et al. "ChatGPT and large language model (LLM) chatbots: the current state of acceptability and a proposal for guidelines on utilization in academic medicine." Journal of Pediatric Urology (2023). (Year: 2023).*

(Continued)

*Primary Examiner* — Christopher B Tokarczyk (74) *Attorney, Agent, or Firm* — Shumaker, Loop & Kendrick, LLP (57) ABSTRACT

A system and a method for generating a medical knowledge packet in an active conversation session. The system receives a message associated with a conversation thread. The system determines a context of the message using a machine learning model. Further, one or more medical knowledge packets from one or more sources may be generated based on the message and the context. A confidence score to the medical knowledge packet is assigned based on one or more factors comprising relevance, accuracy, the one or more sources, and recency of the medical knowledge packet. The medical knowledge packet with a highest confidence score is modified by formatting, summarizing, highlighting, cross-referencing, and simplifying by using one or more text analysis algorithms.

16 Claims, 6 Drawing Sheets

(56) References Cited

U.S. PATENT DOCUMENTS

| | | | | |
|---|---|---|---|---|
| 2012/0253139 | A1* | 10/2012 | Maman | G16H 70/40 |
| | | | | 600/300 |
| 2012/0301864 | A1* | 11/2012 | Bagchi | G09B 7/02 |
| | | | | 434/362 |
| 2018/0322954 | A1* | 11/2018 | Ding | G16H 70/60 |
| 2020/0097814 | A1* | 3/2020 | Devesa | G10L 15/1815 |
| 2020/0117857 | A1* | 4/2020 | Gnanasambandam | |
| | | | | G16H 10/20 |
| 2021/0182709 | A1 | 6/2021 | Manchanda et al. | |
| 2021/0287800 | A1* | 9/2021 | Ghosh | G16H 10/60 |
| 2023/0245774 | A1* | 8/2023 | Sayapaneni | G16H 50/30 |
| | | | | 704/9 |

OTHER PUBLICATIONS

Kaur, Gagandeep, and Amit Sharma. "AI/ML Sentiment Analysis Model for Medical Chatbot: a Review." 2022 Algorithms, Computing and Mathematics Conference (ACM). IEEE, 2022. (Year: 2022).*

* cited by examiner

GENERATING A MEDICAL KNOWLEDGE PACKET IN AN ACTIVE CONVERSATION SESSION

PRIORITY INFORMATION

The present application does not claim a priority from any other application.

TECHNICAL FIELD

The present subject matter described herein, in general, relates to healthcare technology and, more specifically, to a method for generating a medical knowledge packet in an active conversation session.

BACKGROUND

In the healthcare industry, medical professionals converse with patients and exchange information related to patient care, treatments, medical conditions, and other related topics. However, accessing and retrieving relevant medical knowledge during these conversations can be time-consuming and cumbersome.

Traditional approaches rely on manual searches through medical books, guidelines, and various online sources, which can lead to delays and potential inaccuracies. Moreover, the vast amount of medical information available makes it challenging for healthcare professionals to stay up to date with the latest developments and guidelines. Thus, there is a need for an improved system that can help medical professionals and patients with the appropriate medical knowledge in an active conversation.

SUMMARY

Before the present system(s) and method(s), are described, it is to be understood that this application is not limited to the particular system(s), and methodologies described, as there can be multiple possible embodiments which are not expressly illustrated in the present disclosures. It is also to be understood that the terminology used in the description is for the purpose of describing the particular implementations or versions or embodiments only and is not intended to limit the scope of the present application. This summary is provided to introduce aspects related to a system and a method for generating a medical knowledge packet in an active conversation session. This summary is not intended to identify essential features of the claimed subject matter, nor is it intended for use in determining or limiting the scope of the claimed subject matter.

In one implementation, a method for generating a medical knowledge packet in an active conversation session (thread) is disclosed. A message associated with a conversation thread may be received. A context of the message may be determined using a machine learning model. Further, one or more medical knowledge packets may be generated from one or more sources based on the message and the context. The one or more sources may comprise a prestored medical library and external data sources. The prestored medical library may comprise at least one of a medical book, medical guidelines, a medical calculator, medical procedures reference, medical skills information, video, and therapeutic algorithm. The medical knowledge packet may comprise at least one of a medical condition, a medication, a treatment plan, a diagnostic protocol, and a medical definition. Subsequently, a confidence score may be assigned to the medical knowledge packet from the one or more medical knowledge packets based on one or more factors. The one or more factors may comprise relevance, accuracy, the one or more sources, and recency of the medical knowledge packet. Further, the medical knowledge packet with a highest confidence score may be modified by at least one of formatting, summarizing, highlighting, cross-referencing, and simplifying by using one or more text analysis algorithms. Further, the modified medical knowledge packet may be displayed. In one aspect, the aforementioned method for generating a medical knowledge packet in an active conversation session may be performed by a processor using programmed instructions stored in a memory.

In another implementation, a non-transitory computer-readable medium embodying a program executable in a computing device for generating a medical knowledge packet in an active conversation session is disclosed. The program may comprise a program code for receiving a message associated with a conversation thread. The program may comprise a program code for determining a context of the message using a machine learning model. The program may comprise a program code for generating one or more medical knowledge packets from one or more sources based on the message and the context. The one or more sources may comprise a prestored medical library and external data sources. The prestored medical library may comprise at least one of medical book, medical guidelines, medical calculator, medical procedures reference, medical skills information, video, and therapeutic algorithm. The medical knowledge packet may comprise at least one of a medical condition, a medication, a treatment plan, a diagnostic protocol, and a medical definition. The program may comprise a program code for assigning a confidence score to the medical knowledge packet from the one or more medical knowledge packets based on one or more factors. The one or more factors may comprise relevance, accuracy, the one or more sources, and recency of the medical knowledge packet. The program may comprise a program code for modifying the medical knowledge packet with a highest confidence score by at least one of formatting, summarizing, highlighting, cross-referencing, and simplifying by using one or more text analysis algorithms. Further, the program may comprise a program code for displaying the modified medical knowledge packet.

In an embodiment, the program may comprise a program code for updating the prestored medical library based on at least one of a new medical knowledge packet and feedback associated with the one or more factors of previously displayed medical knowledge packets.

BRIEF DESCRIPTION OF THE DRAWINGS

The foregoing detailed description of embodiments is better understood when read in conjunction with the appended drawings. For the purpose of illustrating of the present subject matter, an example of a construction of the present subject matter is provided as figures. However, the invention is not limited to the specific method and system for generating a medical knowledge packet in an active conversation session disclosed in the document and the figures.

The present subject matter is described in detail with reference to the accompanying figures. In the figures, the left-most digit(s) of a reference number identifies the figure in which the reference number first appears. The same numbers are used throughout the drawings to refer to various features of the present subject matter.

The figure depicts an embodiment of the present disclosure for purposes of illustration only. One skilled in the art will readily recognize from the following discussion that alternative embodiments of the structures and methods illustrated herein may be employed without departing from the principles of the disclosure described herein.

DETAILED DESCRIPTION

Some embodiments of this disclosure, illustrating all its features, will now be discussed in detail. The words "receiving," "determining," "identifying," "generating," "assigning," "modifying," "displaying," and other forms thereof, are intended to be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise. Although any system and methods similar or equivalent to those described herein can be used in the practice or testing of embodiments of the present disclosure, the exemplary, system and methods are now described.

The disclosed embodiments are merely examples of the disclosure, which may be embodied in various forms. Various modifications to the embodiment will be readily apparent to those skilled in the art and the generic principles herein may be applied to other embodiments. However, one of ordinary skill in the art will readily recognize that the present disclosure is not intended to be limited to the embodiments described but is to be accorded the widest scope consistent with the principles and features described herein.

The present subject matter discloses a method and a system for generating a medical knowledge packet in an active conversation session. The method may comprise receiving a message associated with a conversation thread and determining a context of the message using a machine learning model. Based on the determined context, one or more medical knowledge packets are generated using one or more sources. The one or more sources may include a prestored medical library and external data sources.

The prestored medical library may comprise a comprehensive collection of medical resources such as medical books, guidelines, calculators, procedures references, skills information, videos, and therapeutic algorithms. The prestored medical library covers a wide range of medical topics and provides valuable information related to medical conditions, medications, treatment plans, diagnostic protocols, and medical definitions.

Further, the generated medical knowledge packets are assigned a confidence score based on several factors, including relevance, accuracy, the sources utilized, and the recency of the information. The confidence score ensures that the most reliable and updated medical knowledge is prioritized for display.

In an embodiment, the method may comprise modifying the medical knowledge packet with the highest confidence score. The modification may involve formatting, summarizing, highlighting, cross-referencing, and simplifying the medical knowledge packet using text analysis algorithms.

Subsequently, the modified medical knowledge packet is displayed to the user. The user may access the medical knowledge packet during the active conversation session, gaining valuable medical insights and information. The displayed medical knowledge packet may also include hyperlinks to the original sources of the information, allowing users to explore further details and verify the provided information.

Figure 1:
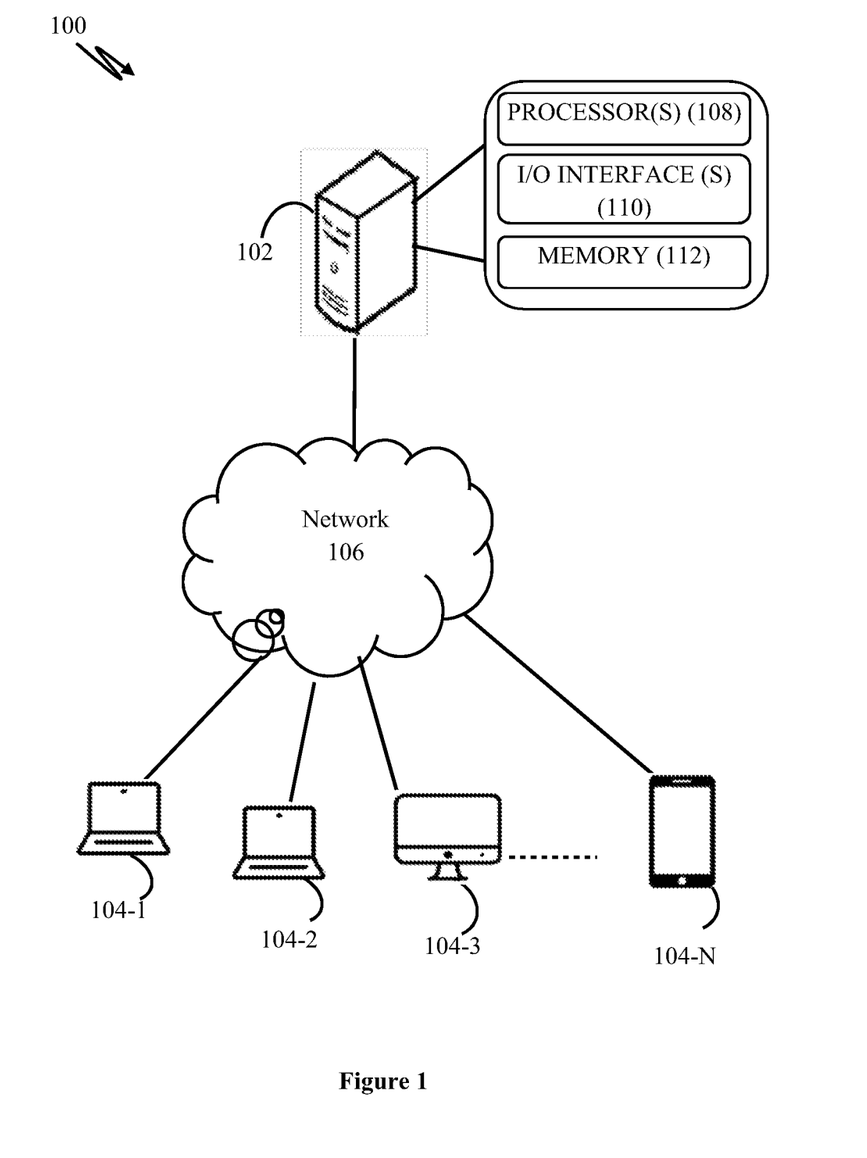
FIG. 1 illustrates a network implementation for generating a medical knowledge packet in an active conversation session, in accordance with an embodiment of the present subject matter.

Referring now to FIG. 1, a network implementation 100 of a system 102 for generating a medical knowledge packet in an active conversation session is disclosed. Initially, the system 102 receives a message associated with a conversation thread. In an example, a messaging software may be installed on a user device 104-1. It may be noted that the one or more users may access the system 102 through one or more user devices 104-2, 104-3 . . . 104-N, collectively referred to as user devices 104, hereinafter, or applications residing on the user devices 104. The system 102 receives a message associated with a conversation thread from one or more user devices 104. Further, the system may also 102 receive a feedback from a user using the user devices 104.

Although the present disclosure is explained considering that the system 102 is implemented on a server, it may be understood that the system 102 may be implemented in a variety of computing systems, such as a laptop computer, a desktop computer, a notebook, a workstation, a virtual environment, a mainframe computer, a server, a network server, a cloud-based computing environment. It will be understood that the system 102 may be accessed by multiple users through one or more user devices 104-1, 104-3 . . . 104-N. In one implementation, the system 102 may comprise the cloud-based computing environment in which the user may operate individual computing systems configured to execute remotely located applications. Examples of the user devices 104 may include, but are not limited to, a portable computer, a personal digital assistant, a handheld device, a display terminal in a vehicle, and a workstation. The user devices 104 are communicatively coupled to the system 102 through a network 106.

In one implementation, the network 106 may be a wireless network, a wired network, or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network

106 may include a variety of network devices, including routers, bridges, servers, computing devices, storage devices, and the like.

In one embodiment, the system 102 may include at least one processor 108, an input/output (I/O) interface 110, and a memory 112. The at least one processor 108 may be implemented as one or more microprocessors, microcomputers, microcontrollers, digital signal processors, Central Processing Units (CPUs), state machines, logic circuitries, and/or any devices that manipulate signals based on operational instructions. Among other capabilities, the at least one processor 108 is configured to fetch and execute computer-readable instructions stored in the memory 112.

The I/O interface 110 may include a variety of software and hardware interfaces, for example, a web interface, a graphical user interface, and the like. The I/O interface 110 may allow the system 102 to interact with the user directly or through the client devices 104. Further, the I/O interface 110 may enable the system 102 to communicate with other computing devices, such as web servers and external data servers (not shown). The I/O interface 110 can facilitate multiple communications within a wide variety of networks and protocol types, including wired networks, for example, LAN, cable, etc., and wireless networks, such as WLAN, cellular, or satellite. The I/O interface 110 may include one or more ports for connecting a number of devices to one another or to another server.

The memory 112 may include any computer-readable medium or computer program product known in the art including, for example, volatile memory, such as static random access memory (SRAM) and dynamic random access memory (DRAM), and/or non-volatile memory, such as read only memory (ROM), erasable programmable ROM, flash memories, hard disks, Solid State Disks (SSD), optical disks, and magnetic tapes. The memory 112 may include routines, programs, objects, components, data structures, etc., which perform particular tasks or implement particular abstract data types. The memory 112 may include programs or coded instructions that supplement applications and functions of the system 102. In one embodiment, the memory 112, amongst other things, serves as a repository for storing data processed, received, and generated by one or more of the programs or the coded instructions.

As there are various challenges observed in the existing art, the challenges necessitate the need to build the system 102 for generating a medical knowledge packet in an active conversation session. At first, a user may use the user device 104 to access the system 102 via the I/O interface 110. The user may register the user devices 104 using the I/O interface 110 in order to use the system 102. In one aspect, the user may access the I/O interface 110 of the system 102. The detail functioning of the system 102 is described below with the help of figures.

The present subject matter discloses a system 102 for generating a medical knowledge packet in an active conversation session. Initially, the system may receive a message associated with a conversation thread. In an example, the conversation thread may involve one or more users, such as doctors, patients, nurses, or other healthcare service providers. In another embodiment, the conversation thread may be a session of messages shared between a group of healthcare users, formed to discuss matters related to medical care. The message may be received in such a conversation thread.

The conversation may be related to health of the patient. It may be noted that the system enables the patient and the doctor along with other care providers to engage in real-time conversations, allowing them to exchange information regarding the patient's condition, treatment plans, and overall well-being.

The system may be accessed by one or more users, catering to different roles, such as patients, doctors, and healthcare providers. Each user who is involved in the conversation is granted access to specific features and functionalities based on their assigned role within the system.

In an embodiment, user interface (UI) of the software may be designed differently for each role type to ensure a customized experience based on user's specific needs and responsibilities. For example, a patient's UI may have options for accessing their personal health data, upcoming appointments with a doctor, and an option to chat with a doctor or healthcare service provider. Further, a doctor's UI may have options for accessing patient records and review their medical history, chief complaints, and current medications. Doctors may engage in real-time conversations with patients and other healthcare providers.

When a user, designated as a patient, logs in to the system, the system may prompt the patient to provide data, including login information, to establish their identity within the system. Additionally, the patient may authorize the health care service providers in the conversation thread to access information related to the patient when necessary. The patient data may be securely stored in the memory 112.

In an embodiment, the system may enrich the patient data by accessing one or more healthcare databases. The enrichment may comprise dynamically retrieving medical information of the patient, including their medical history, chief complaints, current medications, filtered conversations between doctors, structured data from electronic medical records, and longitudinal patient history records from third-party software. The patient record from other medical databases as described herein, associated with the patient may be programmatically linked with the conversation to ease the access of relevant information when necessary.

For example, let's consider a patient named John who logs into the system. The system receives John's data (patient data), including login information, to establish his identity. Further, the system enriches John's patient data by accessing one or more healthcare databases. The system may obtain various medical information about John comprising medical history, chief complaints, current medications, filtered encounter notes, structured data from electronic medical records, and longitudinal patient history records from third-party software. The various medical information is explained below:

Medical History: The system retrieves John's complete medical history, including past diagnoses, treatments, surgeries, and medical procedures John has undergone.

Chief Complaints: The system gathers John's current and past chief complaints, helping to identify recurring health issues or specific symptoms he has experienced.

Current Medications: The system captures a list of medications that John is currently taking, including dosage instructions and any reported side effects.

Filtered Encounter Notes: The system analyzes and filters conversations between John and his previous healthcare providers, extracting valuable insights, treatment recommendations, and relevant medical advice discussed during these interactions. It may be noted that the system does not capture the whole conversation. The system only captures part of the conversation which is related to medication, or the current treatment or care plan identified from the context.

Structured Data from Electronic Medical Records: The system accesses John's electronic medical records (EMRs), extracting structured data such as laboratory results, imaging reports, vital signs, and other relevant clinical data.

Longitudinal Patient History Records from Third-Party Software: The system integrates with third-party software that maintains longitudinal patient history records. The system retrieves and consolidates John's historical health information from these sources. The system gathers information about any previous hospitalizations John has had, including admission dates, discharge summaries, and relevant medical reports.

Further to receiving the message, the system 102 may determine a context of the message using a machine learning model. The machine learning model may be a deep learning model trained to determine the context of the message. In another embodiment, artificial intelligence techniques involving large language models may be used to determine the context of the message. In an embodiment, the context may be at least one of, but not limited to, consultation, prescription, diagnostic, medical term information, symptoms, and treatment plans. In an embodiment, the system may also take day, time, linked/bridged information to retrieve properties from external sources for determining the context.

Some embodiments of the system 102 may utilize a software application that includes a widget named "Lightning™." When a user interacts with the Lightning widget by clicking on it, the system instantly analyzes the message and determines the context of the message.

In another embodiment, the system is designed to analyze the context of the message and generate a medical knowledge packet specifically when the user expresses a need for information related to a specific medical field discussed in the conversation.

In an example, the system may monitor the conversation thread to identify keywords that indicate the user's intent to seek medical knowledge. For instance, if the user mentions terms like "diagnosis," "treatment," or refers to a specific medical condition or medication, it may automatically trigger the system to analyze the context. The system may have a database of one or more keywords related to medical knowledge. In an embodiment, when the system determines that the keyword used in the conversation is from the one or more keywords the system may analyze the context. The context may correspond to an objective of the conversation. For example, let us consider that the conversation comprises a message saying, "please share symptoms of a disease A." The system may analyze the conversation and determine the context as "information request." Similarly, other examples of contexts could be information sharing, diagnosis, checkup scheduling, etc.

Further to determining the context, the system 102 may generate one or more medical knowledge packets from one or more sources based on the message and the context. The medical knowledge packet may comprise at least one of a medical condition, a medication, a treatment plan, a diagnostic protocol, and a medical definition. The one or more sources may comprise a prestored medical library and external data sources.

The prestored medical library may comprise at least one of a medical book, medical guidelines, a medical calculator, medical procedures reference, medical skills information, video, and a therapeutic algorithm. Further, the external data sources may comprise articles, medical journals, blogs, and scientific studies available on the internet. Further, each source of the external data sources may be assigned a weightage based on properties of the source. The properties or attributes of the source may comprise, but not limited to, author's reputation, an update frequency of the source, peer reviews and ratings of information obtained from the source.

In an embodiment, the prestored medical library may be updated based on at least one of when a new medical knowledge packet is available, and feedback associated with the one or more factors of previously displayed medical knowledge packets. The new medical knowledge packet refers to medical information or content that is not present in the system's prestored medical library. This information is retrieved from external sources, such as the internet or new medical books, during an active conversation session in response to a user's query.

When a user sends a message associated with a conversation thread to the system, the system processes the message and uses a machine learning model to determine its context. Based on this context and the user's query, the system generates one or more medical knowledge packets from different sources, including the prestored medical library and external data sources. When the system does not find the required medical information in the prestored medical library, the system may search for the required medical information in external sources. This search may include querying medical journals, articles, blogs, scientific studies, or other reputable online resources to obtain up-to-date and relevant medical knowledge related to the user's query. The information obtained from the external sources may be referred to as a "New Medical Knowledge Packet." It represents the latest and most current medical information available at the time of the user's query. While this information is not part of the system's prestored medical library, it can be considered authoritative and valuable, as it comes from reputable sources and is based on the most recent medical research and knowledge. The system may present the new medical knowledge packet to the user as part of the generated responses to the user's query. Additionally, the system may choose to store the new medical knowledge packet for future use and consider adding the new medical knowledge packet to the prestored medical library after validating its accuracy and relevance.

It may be noted that the system may generate a custom medical knowledge packet for a patient based on the enriched patient data comprising patient's prescription data, medical history, and previous conversations.

In an embodiment, the generated medical knowledge packet may be saved as a template for future use and modification. This feature allows medical professionals to create standardized templates based on specific medical conditions, treatments, or protocols that they frequently encounter. When a Medical Packet is saved as a Template, the system provides a user-friendly interface that allows editing and updating of certain sections within the template. These sections are designed to be changeable or blank, and the UI presents a Form substitution fashion, making it straightforward for users to input relevant information when using the template for different cases. For instance, certain fields within the template, such as patient-specific details, dosage information, or treatment duration, might vary from case to case. The system enables users to identify these variable fields to be automatically populated by filling in the relevant information before disseminating the template to other system users or external parties, such as insurance companies, patients, or their families, if required.

This functionality streamlines the process of creating medical documents, ensuring consistency and accuracy in the information presented. It also enhances efficiency, as medical professionals can leverage pre-existing templates rather than creating documents from scratch each time.

Furthermore, the ability to customize certain fields within the template adds a layer of flexibility, allowing medical professionals to tailor the information to specific patient needs or unique cases.

Consider an example, a patient and a doctor are having a conversation. The system receives a message associated with the conversation. Let us assume that the message from the patient is, "I'm experiencing chest pain and shortness of breath." The system may analyze the message and determine the context that the patient is describing symptoms related to a potential cardiovascular issue. Further, based on the message and the context, the system may generate one or more medical knowledge packets with relevant information.

In an embodiment, the system may generate one or more types of medical knowledge packets. Below are a few examples of the one or more type of medical knowledge packets:

A) Medical Knowledge Packet: Medical Condition

Description: The patient's symptoms of chest pain and shortness of breath may indicate a potential cardiovascular condition.

Possible Causes: The medical knowledge packet provides information on various causes of chest pain and shortness of breath, including heart attack, angina, pulmonary embolism, and other cardiac-related conditions.

Recommended Actions: The packet suggests seeking immediate medical attention, contacting emergency services, or consulting a healthcare professional for proper evaluation and diagnosis.

B) Medical Knowledge Packet: Treatment Plan

Description: The packet provides a general overview of treatment options for cardiovascular conditions based on the patient's symptoms.

Recommended Treatments: The packet outlines possible treatments, such as medications, lifestyle modifications (e.g., diet, exercise), and potential interventions (e.g., angioplasty, bypass surgery) that may be considered based on the specific diagnosis and severity of the condition.

C) Medical Knowledge Packet: Diagnostic Protocol

Description: The packet explains the diagnostic process for evaluating chest pain and shortness of breath in a suspected cardiovascular context.

Diagnostic Tests: The packet mentions common diagnostic tests that may be conducted, such as electrocardiogram (ECG/EKG), stress test, echocardiogram, blood tests (e.g., cardiac enzymes, lipid profile), and potentially advanced imaging techniques (e.g., angiography).

Importance of Evaluation: The packet emphasizes the importance of seeking medical evaluation and undergoing diagnostic tests to determine the underlying cause and guide appropriate treatment.

It may be noted that the above one or more types of knowledge packets may be generated for the doctor or the patient. In the example, the system generates the one or more types of knowledge packets for the doctor based on the conversation with the patient and the patient's data.

Further to generating the one or more medical knowledge packets, the system 102 may assign a confidence score to each medical knowledge packet from the one or more medical knowledge packets. The confidence score is assigned based on one or more factors comprising relevance, accuracy, the one or more sources, and recency of the medical knowledge packet. In an example, and not by way of any limitation, the system may utilize a confidence scoring model for assigning a confidence score to each medical knowledge packet. The confidence scoring model may be at least one of a weighted scoring model, Bayesian Interference model, Support Vector Machines (SVM), Neural Networks, and Rule-based model.

In an example, let us assume that the system generates one or more medical knowledge packets for a message/query, received from the doctor, related to Atrial Fibrillation. Below are the examples of the one or more medical knowledge packets:

Medical Knowledge Packet 1: Atrial Fibrillation Definition

Description: This packet provides a clear and concise definition of atrial fibrillation.

Definition: Atrial fibrillation is a cardiac arrhythmia characterized by irregular and rapid electrical signals in the atria of the heart, resulting in an irregular and often rapid heartbeat.

Reference: The definition is sourced from the book "Cardiac Arrhythmias: Understanding and Management" by John Smith, Chapter 2, Topic "Valve Disorders".

Medical Knowledge Packet 2: Atrial Fibrillation Explained

Description: This packet offers a comprehensive explanation of atrial fibrillation.

Explanation: Atrial fibrillation is a condition where the electrical signals in the atria of the heart become chaotic, causing the atria to quiver instead of contracting effectively.

This leads to an irregular heartbeat and can disrupt the normal blood flow through the heart.

Reference: The explanation is sourced from the book "Understanding Cardiac Arrhythmias" by Jane Doe, Chapter 4, Topic "Cardiomyopathy".

Medical Knowledge Packet 3: Atrial Fibrillation Overview

Description: This packet provides an overview of atrial fibrillation, highlighting its key characteristics.

Overview: Atrial fibrillation is an abnormal heart rhythm that arises from the atria. It is characterized by rapid, irregular electrical impulses that can result in a fast and irregular heartbeat. It is one of the most common cardiac arrhythmias and can increase the risk of stroke and other complications.

Reference: The information is sourced from the book "Cardiac Electrophysiology: An Illustrated Guide" by Robert Johnson, Chapter 3, Topic "Heart Valve Disease".

In the example, the system may assign a confidence score to the one or more medical knowledge packets. The below tables illustrate an example of the confidence score:

| Knowledge Packet | Confidence Score |
| --- | --- |
| Medical Knowledge Packet 1 | 0.8 |
| Medical Knowledge Packet 2 | 0.7 |
| Medical Knowledge Packet 3 | 0.9 |

Medical Knowledge Packet 3 has the highest score because the overview is highly relevant, accurate, and sourced from a reputable book on cardiac electrophysiology. It covers key aspects of Atrial Fibrillation and is relatively recent, increasing its confidence score.

Further to assigning the confidence score, the system may modify the medical knowledge packet with a highest confidence score. The modification may comprise formatting, summarizing, highlighting, cross-referencing, and simplifying of the medical knowledge packet by using one or more text analysis algorithms. In an embodiment, the one or more knowledge packets with the confidence score greater than a predefined threshold are also modified.

In the above example, the system may modify the Medical Knowledge Packet 3. The modified medical knowledge packet may be as below:

Modified Version: Atrial Fibrillation Definition

Definition: Atrial fibrillation (AF) is an irregular and rapid heart rhythm disorder that affects the atria, the upper chambers of the heart. It is characterized by chaotic electrical signals, causing the atria to quiver instead of contracting normally. This results in an irregular heartbeat and can lead to symptoms such as palpitations, shortness of breath, and fatigue. AF increases the risk of blood clots, which can travel to the brain and cause a stroke.

The modification process involves formatting the information to enhance readability, summarizing the key points, highlighting important details, and simplifying the language for better understanding. Text analysis algorithms were utilized to identify and optimize the presentation of relevant information, ensuring a concise and user-friendly medical knowledge packet.

In an alternate embodiment, construe that the system receives a message: "I'm experiencing severe headache and dizziness". Further, the system retrieves the patient data from one or more healthcare databases. Let's assume that the system retrieves that the patient has "a history of taking medication for high blood pressure."

The system may generate a customized medical knowledge packet based on the context and the message. For instance, the customized medical knowledge packet is as mentioned below:

Title—"Possible Causes of Severe Headache and Dizziness"

Overview: Severe headache and dizziness can have various underlying causes. Here are some possible causes to consider:

Migraine: Migraine headaches can cause severe head pain accompanied by dizziness, nausea, and sensitivity to light and sound. They can be triggered by certain foods, stress, hormonal changes, or environmental factors.

Vestibular Disorders: Disorders affecting the inner ear or vestibular system can result in dizziness and vertigo, which may be accompanied by headaches. Examples include Meniere's disease, vestibular migraine, or benign paroxysmal positional vertigo (BPPV).

High Blood Pressure: Hypertension (high blood pressure) can lead to headaches and dizziness. If you have a history of taking medication for high blood pressure, it is important to monitor your blood pressure levels and inform your healthcare provider.

Medication Side Effects: Some medications, including those used for high blood pressure, can cause headaches and dizziness as side effects. It is advisable to review the medications you are currently taking and discuss any concerns with your healthcare provider.

Further, the system may modify the medical knowledge packet by applying text analysis algorithms. The modified medical knowledge is displayed to the patient in the below manner:

Title: Possible Causes of Severe Headaches and Dizziness

Overview: Severe headaches and dizziness can have various underlying causes. Here are some potential reasons to consider:

Migraine: Intense head pain accompanied by dizziness, nausea, and sensitivity to light and sound. Triggers: certain foods, stress, hormonal changes, or environmental factors.

Vestibular Disorders: Inner ear or vestibular system issues causing dizziness, vertigo, and headaches. Examples: Meniere's disease, vestibular migraine, or BPPV.

High Blood Pressure: Hypertension leading to headaches and dizziness. If you have a history of taking medication for high blood pressure, it is important to monitor your blood pressure levels and inform your healthcare provider for appropriate management.

Medication Side Effects: Some medications, including those used for high blood pressure, may result in headaches and dizziness. Review your current medications and discuss any concerns with your healthcare provider.

In the above example, the system modifies the medical knowledge packet by including specific details related to the patient's history of taking medication for high blood pressure. Further, irrelevant details have been removed, and the content has been presented in a concise and easy-to-understand format. Additionally, important keywords may be highlighted for better readability and comprehension.

Further to modification of the medical knowledge packet, the system 102 may display the modified medical knowledge packet to the user. The user may be one of a doctor, patient, nurse, and a healthcare service provider. The medical knowledge packet is displayed along with a hyperlink to the original source of the information.

Figure 2:
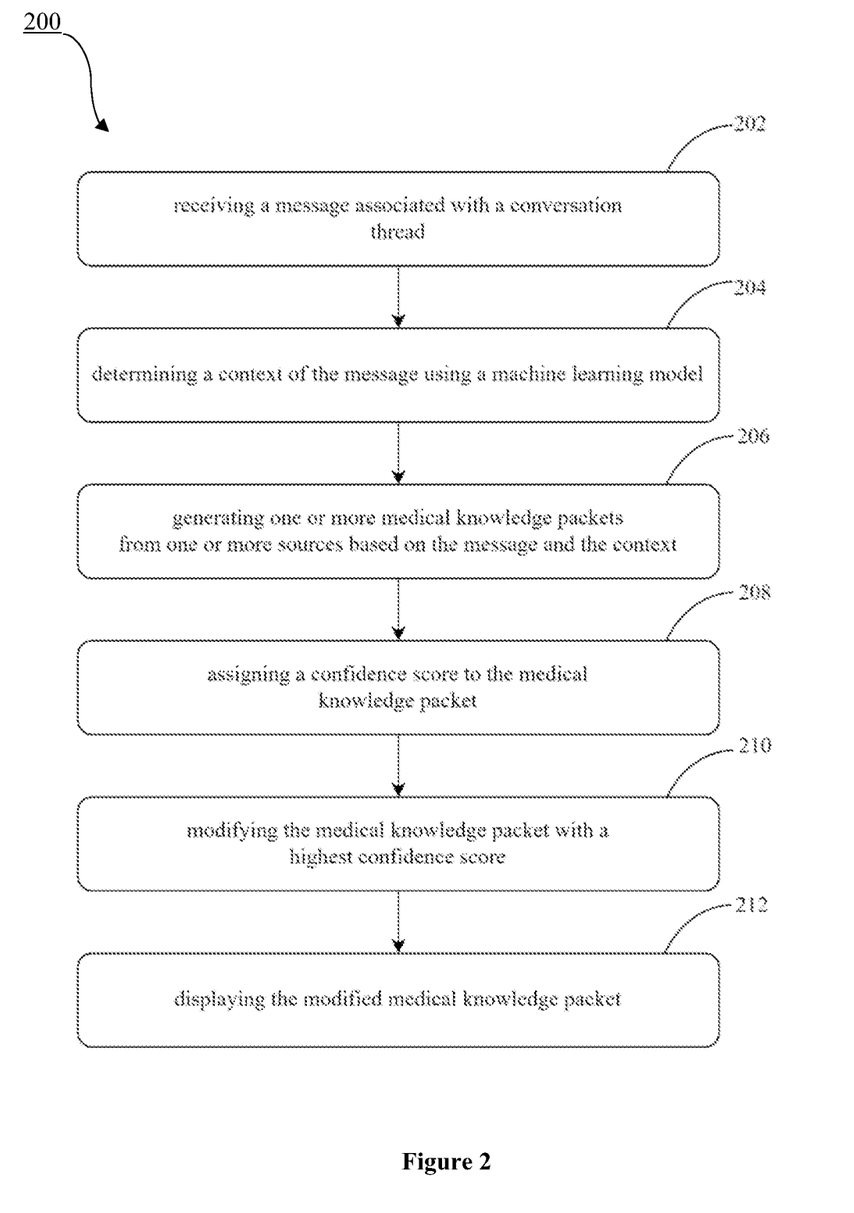
FIG. 2 illustrates a method for generating a medical knowledge packet in an active conversation session, in accordance with an embodiment of the present subject matter.

Referring now to FIG. 2, a method 200 for generating a medical knowledge packet in an active conversation session is shown, in accordance with an embodiment of the present subject matter. The method 200 may be described in the general context of computer executable instructions. Generally, computer executable instructions can include routines, programs, objects, components, data structures, procedures, modules, functions, etc., that perform particular functions or implement particular abstract data types.

The order in which the method 200 is described is not intended to be construed as a limitation, and any number of the described method blocks can be combined in any order to implement the method 200 or alternate methods for generating a medical knowledge packet in an active conversation session. Additionally, individual blocks may be deleted from the method 200 without departing from the scope of the subject matter described herein. Furthermore, the method 200 for generating a medical knowledge packet in an active conversation session can be implemented in any suitable hardware, software, firmware, or combination thereof. However, for ease of explanation, in the embodiments described below, the method 200 may be considered to be implemented in the above-described system 102.

At block 202, a message associated with a conversation thread may be received.

At block 204, a context of the message may be determined using a machine learning model. The machine learning may include a large language model. The large language model may be fine-tuned by providing a domain-specific dataset comprising a medical text, a medical conversation, a medical knowledge source, medical question answering data, a medical record, and a medical report. In an embodiment, the system may also take day, time, linked/bridged information to retrieve properties from external sources for determining the context.

At block 206, one or more medical knowledge packets may be generated from one or more sources based on the message and the context. The one or more sources may comprise a prestored medical library and external data sources. The prestored medical library comprises at least one of a medical book, medical guidelines, a medical calculator, medical procedures reference, medical skills information, video, and therapeutic algorithm. The medical knowledge packet may comprise at least one of a medical condition, a medication, a treatment plan, a diagnostic protocol, and a medical definition. The external data sources may comprise articles, medical journals, blogs, and scientific studies available on internet. In an embodiment, the one or more sources may be assigned weightages. In an embodiment the weightages may be predefined. In another embodiment, the weightages for the external data sources may be dynamic. The system may update the weightages for the external data sources based on one or more factors including comments, number of views, ratings, and the like.

At block 208, a confidence score may be assigned to the medical knowledge packet from the one or more medical knowledge packets based on one or more factors comprising relevance, accuracy, the one or more sources, and recency of the medical knowledge packet.

At block 210, the medical knowledge packet with a highest confidence score may be modified by at least one of formatting, summarizing, highlighting, cross-referencing, and simplifying by using one or more text analysis algorithms. The one or the text analysis algorithms may comprise at least one of Natural Language Processing (NLP) based algorithms, text segmentation algorithms, and summarization algorithms.

At block 212, the modified medical knowledge packet may be displayed on an interface of a user device. The user may be one of a doctor, patient, nurse, or a medical practitioner. The medical knowledge packet is displayed along with a hyperlink to the original source of the information.

Figure 3A:
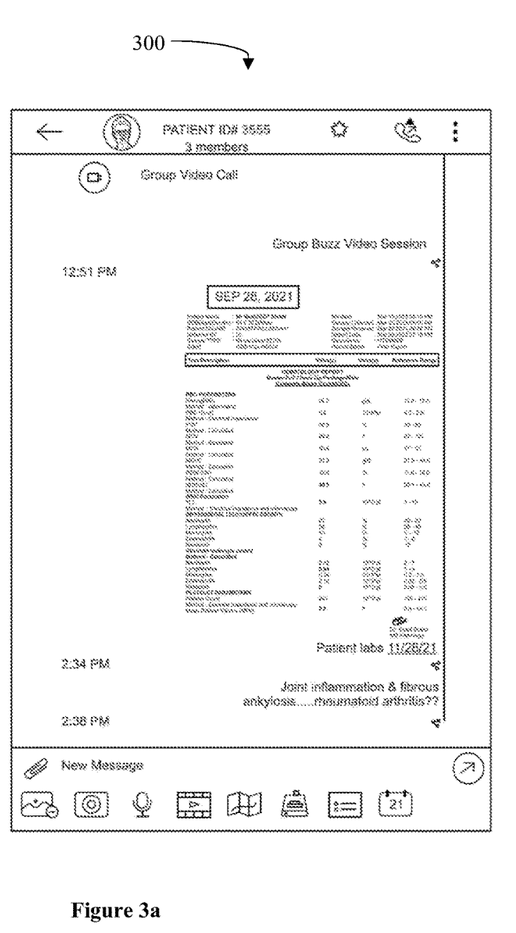
FIGS. 3a, 3b, and 3c illustrate examples of a User Interface (UI) for generating a medical knowledge packet in an active conversation session.
Figure 3B:
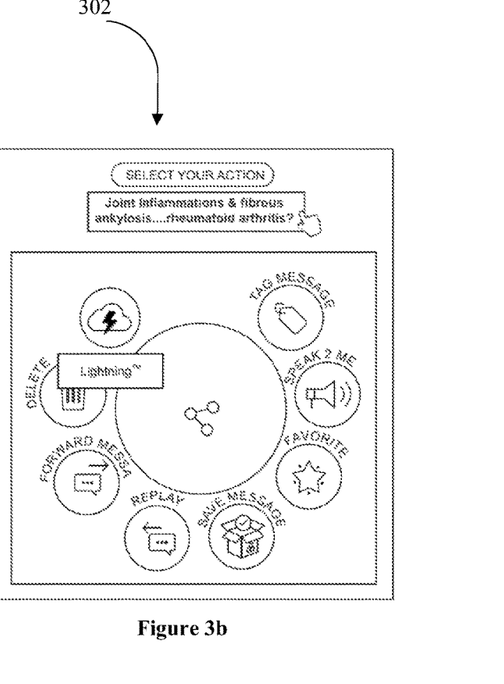
Figure 3C:
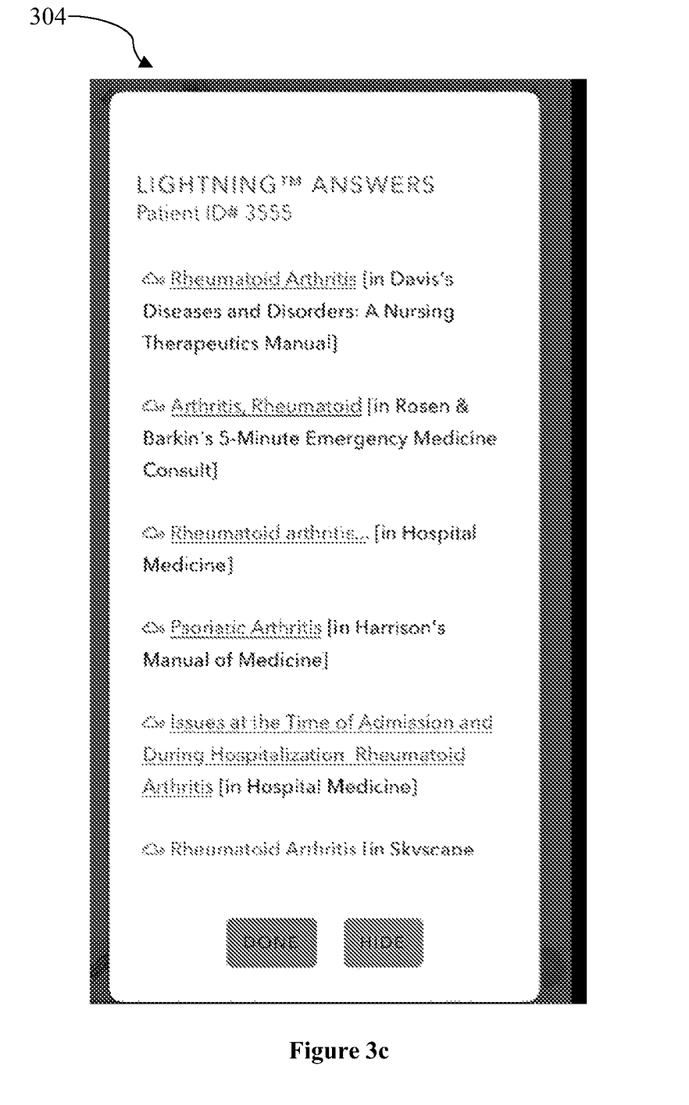

FIGS. 3a, 3b, and 3c illustrate examples (300, 302, 304) of a User Interface (UI) for generating a medical knowledge packet in an active conversation session. FIG. 3a illustrates an active conversation between one or more doctors and care providers in the context of a care of a patient (patient id #3555). Further, FIG. 3a shows a message by the doctor. The message is "Joint inflammation and fibrous ankylosis . . . rheumatoid arthritis??" In the example, the doctor may perform a long press on the displayed message to get one or more actions shown in FIG. 3b. In an alternate embodiment, an icon may be used to provide actions based on the displayed message. In an another embodiment, the actions may be automatically populated and displayed to the user along with the displayed message. FIG. 3b shows the one or more actions that can be performed on the message. Furthermore, FIG. 3b also displays an action icon "Lightning™" to the doctor When the doctor clicks on the lightning icon, the system may generate a medical knowledge packet for the doctor. FIG. 3c displays answers (medical knowledge packets) generated by the system. The answers may be generated by transforming the medical knowledge packet into a predefined format. Further, one or more medical knowledge packets may be transformed and displayed in the order of the confidence score of the medical knowledge packets. In an embodiment, the answer may comprise information related to at least one of a medical condition, a treatment plan, a diagnostic protocol, and the like.

Figure 4:
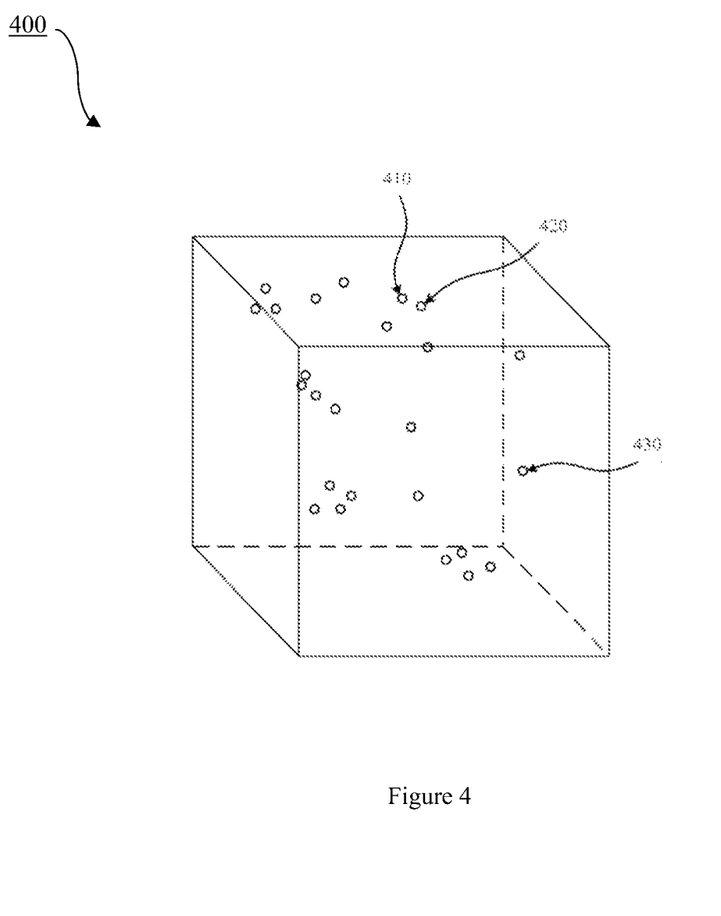
FIG. 4 illustrates an example view of an embedding space, in accordance with an embodiment of the present subject matter.

FIG. 4 illustrates an example view of a vector space 400. In particular embodiments, an object or an n-gram may be represented in a d-dimensional vector space, where d denotes any suitable number of dimensions. In the present invention, the system utilizes a vector space representation to represent objects or n-grams, such as medical terms, keywords, or context elements from conversations. Although the vector space 400 is illustrated as a three-dimensional space, this is for illustrative purposes only, as the vector space 400 may be of any suitable dimension. In particular embodiments, an n-gram may be represented in the vector space 400 as a vector referred to as a term embedding. Each vector may comprise coordinates corresponding to a particular point in the vector space 400 (i.e., the terminal point of the vector). As an example, and not by way of limitation, vectors 410, 420, and 430 may be represented as points in the vector space 400, as illustrated in FIG. 4.

The vector space representation allows the system to capture the relationships and similarities between different objects, enabling efficient processing and retrieval of relevant information. As another example and not by way of limitation, a dictionary trained to map text to a vector representation may be utilized, or such a dictionary may be itself generated via training. As another example and not by way of limitation, a model, such as Word2vec, may be used to map an n-gram to a vector representation in the vector space 400. In particular embodiments, an n-gram may be mapped to a vector representation in the vector space 400 by using a machine leaning model (e.g., a neural network). The machine learning model may have been trained using a sequence of training data (e.g., a corpus of objects each comprising n-grams).

In particular embodiments, an object may be represented in the vector space 400 as a vector referred to as a feature vector or an object embedding. In particular embodiments, an object may be mapped to a vector based on one or more properties, attributes, or features of the object, relationships of the object with other objects, or any other suitable information associated with the object. As an example, one or more keywords from the conversations may be plotted in the vector space. Further, the keywords may be mapped to features such as context to identify the context of a conversation. Each keyword from the conversation may have coordinates in the vector space. Further, the vector space may comprise a dictionary of keywords at predefined coordinates. The contexts for the keywords in the dictionary may be predefined. To determine the context of the keywords from the conversation, the distance between the keywords from the conversation and keywords from the dictionary may be calculated. Further, the context for the keywords from the dictionary closest to the keywords from the conversation may be determined as the context of the conversation.

In particular embodiments, the system 102 may calculate a similarity metric of vectors in vector space 400. A similarity metric may be a cosine similarity, a Minkowski distance, a Mahalanobis distance, a Jaccard similarity coefficient, or any suitable similarity metric. The similarity metric of two vectors may represent how similar the two objects or n-grams corresponding to the two vectors, respectively, are to one another, as measured by the distance between the two vectors in the vector space 400. As an example and not by way of limitation, vector 410 and vector 420 may correspond to objects that are more similar to one another than the objects corresponding to vector 410 and vector 430, based on the distance between the respective vectors. Although this disclosure describes calculating a similarity metric between vectors in a particular manner, this disclosure contemplates calculating a similarity metric between vectors in any suitable manner.

Figure 5:
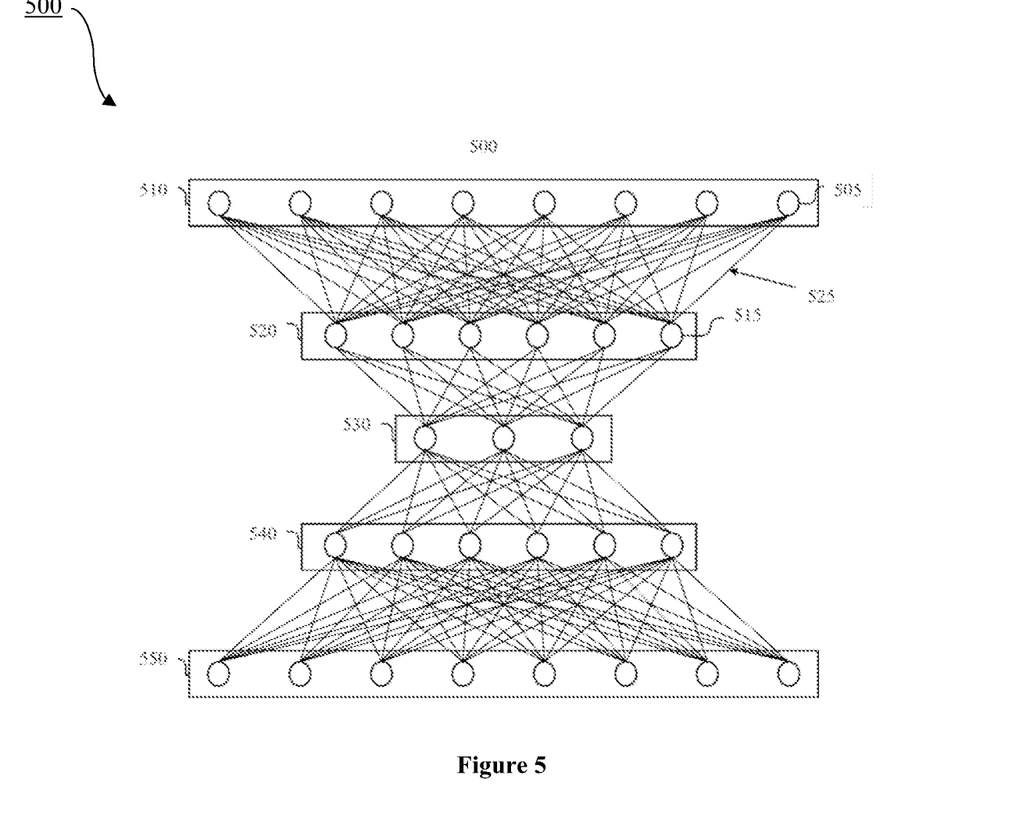
FIG. 5 illustrates an example artificial neural network, in accordance with an embodiment of the present subject matter.

FIG. 5 illustrates an example artificial neural network ("ANN") 500 of the deep learning algorithms. In an embodiment, the ANN may be used to extract features from the messages of the conversations. The features may include context. Each layer of the ANN may be used for different functions, including identifying keywords, identifying connected messages, and determining the context of the conversation. In another embodiment, the ANN may be used to determine a confidence score of the medical knowledge packet. The ANN may be trained using deep learning algorithms. In another embodiment, the ANN may be used to determine confidence score of the medical knowledge packet. In particular embodiments, an ANN may refer to a computational model comprising one or more nodes. Example ANN 500 may comprise an input layer 510, hidden layers 520, 530, 540, and an output layer 550. Each layer of the ANN 500 may comprise one or more nodes, such as a node 505 or a node 515. In particular embodiments, each node of an ANN may be connected to another node of the ANN. As an example and not by way of limitation, each node of the input layer 510 may be connected to one of more nodes of the hidden layer 520. In particular embodiments, one or more nodes may be a bias node (e.g., a node in a layer that is not connected to and does not receive input from any node in a previous layer). In particular embodiments, each node in each layer may be connected to one or more nodes of a previous or subsequent layer. Although FIG. 5 depicts a particular ANN with a particular number of layers, a particular number of nodes, and particular connections between nodes, this disclosure contemplates any suitable ANN with any suitable number of layers, any suitable number of nodes, and any suitable connections between nodes. As an example and not by way of limitation, although FIG. 5 depicts a connection between each node of the input layer 510 and each node of the hidden layer 520, one or more nodes of the input layer 510 may not be connected to one or more nodes of the hidden layer 520.

In particular embodiments, an ANN may be a feedforward ANN (e.g., an ANN with no cycles or loops where communication between nodes flows in one direction beginning with the input layer and proceeding to successive layers). As an example and not by way of limitation, the input to each node of the hidden layer 520 may comprise the output of one or more nodes of the input layer 510. As another example and not by way of limitation, the input to each node of the output layer 550 may comprise the output of one or more nodes of the hidden layer 540. In particular embodiments, an ANN may be a deep neural network (e.g., a neural network comprising at least two hidden layers). In particular embodiments, an ANN may be a deep residual network. A deep residual network may be a feedforward ANN comprising hidden layers organized into residual blocks. The input into each residual block after the first residual block may be a function of the output of the previous residual block and the input of the previous residual block. As an example and not by way of limitation, the input into residual block N may be $F(x)+x$, where $F(x)$ may be the output of residual block N−1, x may be the input into residual block N−1. Although this disclosure describes a particular ANN, this disclosure contemplates any suitable ANN.

In particular embodiments, an activation function may correspond to each node of an ANN. An activation function of a node may define the output of a node for a given input. In particular embodiments, an input to a node may comprise a set of inputs. As an example and not by way of limitation, an activation function may be an identity function, a binary step function, a logistic function, or any other suitable function.

In particular embodiments, the input of an activation function corresponding to a node may be weighted. Each node may generate output using a corresponding activation function based on weighted inputs. In particular embodiments, each connection between nodes may be associated with a weight. As an example and not by way of limitation, a connection 525 between the node 505 and the node 515 may have a weighting coefficient of 0.4, which may indicate that 0.4 multiplied by the output of the node 505 is used as an input to the node 515. In particular embodiments, the input to nodes of the input layer may be based on a vector representing an object. Although this disclosure describes particular inputs to and outputs of nodes, this disclosure contemplates any suitable inputs to and outputs of nodes. Moreover, although this disclosure may describe particular connections and weights between nodes, this disclosure contemplates any suitable connections and weights between nodes.

In particular embodiments, the ANN may be trained using training data. As an example and not by way of limitation, training data may comprise inputs to the ANN 500 and an expected output. As another example and not by way of limitation, training data may comprise vectors each representing a training object and an expected label for each training object. In particular embodiments, training the ANN may comprise modifying the weights associated with the connections between nodes of the ANN by optimizing an objective function. As an example and not by way of limitation, a training method may be used (e.g., the conjugate gradient method, the gradient descent method, the stochastic gradient descent) to backpropagate the sum-of-squares error measured as a distances between each vector representing a training object (e.g., using a cost function that minimizes the sum-of-squares error). In particular embodiments, the ANN may be trained using a dropout technique. As an example and not by way of limitation, one or more nodes may be temporarily omitted (e.g., receive no input and generate no output) while training. For each training object, one or more nodes of the ANN may have some probability of being omitted. The nodes that are omitted for a particular training object may be different than the nodes omitted for other training objects (e.g., the nodes may be temporarily omitted on an object-by-object basis). Although this disclosure describes training the ANN in a particular manner, this disclosure contemplates training the ANN in any suitable manner.

Exemplary embodiments discussed above may provide certain advantages. Though not required to practice aspects of the disclosure, these advantages may include those provided by the following features.

Some embodiments of the method and the system enable the generation of medical knowledge packets in real time during active conversation sessions.

Some embodiments of the method and the system enable the utilization of a machine learning model to determine the context of the message. The context of the message ensures that the generated medical knowledge packets are customized for the conversation. By considering the message content and context, the method provides accurate and relevant medical knowledge packet to a user.

Some embodiments of the method and the system enable assigning confidence scores to the generated medical knowledge packets based on one or more factors such as relevance, accuracy, sources, and recency. By evaluating the one or more factors, the method ensures that the most reliable and up-to-date information is displayed to the users.

Some embodiments of the method and the system enable the generation of custom medical knowledge packets for patients based on the patient's data. The patient data comprises prescription data, medical history, and previous conversations. This personalized approach enhances patient-centered care by providing customized medical information relevant to the individual's requirements.

Some embodiments of the method and the system enable updating of the prestored medical library based on new medical knowledge packets and user feedback. This iterative process ensures that the prestored medical library remains updated by incorporating the latest advancements in the medical field.

Although implementations for methods and system for generating a medical knowledge packet in an active conversation session have been described in language specific to structural features and/or methods, it is to be understood that the appended claims are not necessarily limited to the specific features or methods described. Rather, the specific features and methods are disclosed as examples of implementations for generating a medical knowledge packet in an active conversation session.

The invention claimed is:

1. A method for generating a medical knowledge packet in an active conversation session, the method comprising:
   receiving, by a processor, a message associated with a conversation thread;
   monitoring, by the processor, the conversation thread to identify one or more keywords indicating user's intent to seek medical knowledge whereby upon identification, triggering the processor to determine a context of the message associated with the conversation thread;
   determining, by the processor, the context of the message using a machine learning model based on identification of the one or more keywords in the conversation thread, wherein the machine learning includes a large language model, and wherein the large language model is fine-tuned by providing a domain-specific dataset comprising a medical text, a medical conversation, a medical knowledge source, medical question answering data, a medical record and a medical report;
   generating, by the processor, one or more medical knowledge packets, from one more sources based on the message and the context,
   wherein the one or more data sources comprises a prestored medical library comprising a collection of medical resources and external data sources including third-party software, communicatively coupled with the processor, maintaining patient history records, and wherein the prestored medical library comprises medical books, medical guidelines, medical calculator, medical procedures reference, medical skills information, video, and therapeutic algorithm, and wherein the medical knowledge packet comprises at least one of a medical condition, a medication, a treatment plan, a diagnostic protocol, and a medical definition, and wherein the prestored medical library is updated based on at least one of:
   when a new medical knowledge packet is available; and
   a feedback associated with the one or more factors of previously displayed medical knowledge packets;
   assigning, by the processor, a confidence score to the medical knowledge packet from the one or more medical knowledge packets based on one or more factors comprising relevance, accuracy, the one or more sources, and recency of the medical knowledge packet;
   modifying, by the processor, the medical knowledge packet with a highest confidence score by at least one of formatting, highlighting, and simplifying by using one or more text analysis algorithms; and
   displaying, by the processor, the modified medical knowledge packet in the active conversation session.

2. The method of claim 1, further comprising generating a custom medical knowledge packet for a patient based on patient data comprising patient's prescription data, medical history, and previous conversations.

3. The method of claim 2, further comprising enriching the patient data from one or more healthcare databases by dynamically retrieving medical history of the patient, chief complaints, current medications, past hospitalizations, filtered conversations of the patient, structured information found in electronic medical records, and longitudinal patient history records in a third-party software.

4. The method of claim 2, further comprising identifying an overlapping medical knowledge packet based on historical data of one or more patients having similar context of the message, medical history, and previous conversations.

5. The method of claim 1, further comprising displaying the one or more knowledge packets with the confidence score greater than a predefined threshold.

6. The method of claim 1, wherein the external data sources comprise articles, medical journals, blogs, and scientific studies available on internet.

7. The method of claim 1, wherein the one or more text analysis algorithms comprise at least one of Natural Language Processing (NLP) based algorithms, text segmentation algorithms, and summarization algorithms.

8. The method of claim 1, wherein the one or more sources are assigned a predefined weightage for assigning the confidence score.

9. A system for generating a medical knowledge packet in an active conversation session, the system comprising:
   a memory; and
   a processor coupled to the memory, wherein the processor is configured to execute program instructions stored in the memory for:
   receiving a message associated with a conversation thread;
   monitoring the conversation thread to identify one or more keywords indicating user's intent to seek medical knowledge whereby upon identification, triggering the processor to determine a context of the message associated with the conversation thread;
   determining the context of the message using a machine learning model based on identification of the one or more keywords in the conversation thread wherein the machine learning includes a large language model, and wherein the large language model is fine-tuned by providing a domain-specific dataset comprising a medical text, a medical conversation, a medical knowledge source, medical question answering data, a medical record and a medical report;
   generating one or more medical knowledge packets from one more sources based on the message and the context,
   wherein the one or more data sources comprises a prestored medical library comprising a collection of medical resources and external data sources including third-party software, communicatively coupled with the processor, maintaining patient history records, and wherein the prestored medical library comprises medical books, medical guidelines, medical calculator, medical procedures reference, medical skills information, video, and therapeutic algorithm, and wherein the medical knowledge packet comprises at least one of a medical condition, a medication, a treatment plan, a diagnostic protocol, and a medical definition and wherein the prestored medical library is updated based on at least one of:
when a new medical knowledge packet is available; and
a feedback associated with the one or more factors of previously displayed medical knowledge packets;
assigning a confidence score to the medical knowledge packet from the one or more medical knowledge packets based on one or more factors comprising relevance, accuracy, the one or more sources, and recency of the medical knowledge packet;
modifying the medical knowledge packet with a highest confidence score by at least one of formatting, highlighting, and simplifying by using one or more text analysis algorithms; and
displaying the modified medical knowledge packet in the active conversation session.

10. The system of claim 9, further comprising generating a custom medical knowledge packet for a patient based on patient data comprising patient's prescription data, medical history, and previous conversations.

11. The system of claim 10, further comprising identifying an overlapping medical knowledge packet based on historical data of one or more patients having similar context of the message, medical history, and previous conversations.

12. The system of claim 9, further comprising enriching the patient data from one or more healthcare databases by
dynamically retrieving medical history of the patient, chief complaints, current medications, past hospitalizations, filtered conversations of the patient, structured information found in electronic medical records, and longitudinal patient history records in a third-party software.

13. The system of claim 9 further comprising displaying the one or more knowledge packets with the confidence score greater than a predefined threshold.

14. The system of claim 9 wherein the external data sources comprise articles, medical journals, blogs, and scientific studies available on internet.

15. The system of claim 9 wherein the one or more text analysis algorithms comprise at least one of Natural Language Processing (NLP) based algorithms, text segmentation algorithms, and summarization algorithms.

16. A non-transitory computer program product having embodied thereon a computer program for generating a medical knowledge packet in an active conversation session the computer program product storing instructions for:
receiving, by a processor, a message associated with a conversation thread;
monitoring, by the processor, the conversation thread to identify one or more keywords indicating user's intent to seek medical knowledge whereby upon identification, triggering the processor to determine a context of the message associated with the conversation thread;
determining, by the processor, the context of the message using a machine learning model based on identification of the one or more keywords in the conversation thread, wherein the machine learning includes a large language model, and wherein the large language model is fine-tuned by providing a domain-specific dataset comprising a medical text, a medical conversation, a medical knowledge source, medical question answering data, a medical record and a medical report;
generating, by the processor, one or more medical knowledge packets from one more sources based on the message and the context,
wherein the one or more data sources comprises a prestored medical library comprising a collection of medical resources and external data sources including third-party software, communicatively coupled with the processor, maintaining patient history records, and wherein the prestored medical library comprises medical books, medical guidelines, medical calculator, medical procedures reference, medical skills information, video, and therapeutic algorithm, and wherein the medical knowledge packet comprises at least one of a medical condition, a medication, a treatment plan, a diagnostic protocol, and a medical definition and wherein the prestored medical library is updated based on at least one of:
when a new medical knowledge packet is available; and
a feedback associated with the one or more factors of previously displayed medical knowledge packets;
assigning, by the processor, a confidence score to the medical knowledge packet from the one or more medical knowledge packets based on one or more factors comprising relevance, accuracy, the one or more sources, and recency of the medical knowledge packet;
modifying, by the processor, the medical knowledge packet with a highest confidence score by at least one of formatting, highlighting, and simplifying by using one or more text analysis algorithms; and
displaying, by the processor, the modified medical knowledge packet in the active conversation session.

* * * * *